United States Patent [19]

Adams et al.

[11] Patent Number: 4,520,028

[45] Date of Patent: May 28, 1985

[54] α-AMINOBUTYRIC ACID TRANSAMINASE INHIBITORS

[75] Inventors: Jerry L. Adams, West Chester; Brian W. Metcalf, Mason; Bruce J. Lippert, Cincinnati, all of Ohio

[73] Assignee: Merrell Dow Pharmaceuticals Inc., Cincinnati, Ohio

[21] Appl. No.: 647,867

[22] Filed: Sep. 5, 1984

Related U.S. Application Data

[63] Continuation of Ser. No. 597,786, Apr. 6, 1984, abandoned, which is a continuation of Ser. No. 540,744, Oct. 11, 1983, abandoned.

[51] Int. Cl.$^3$ .................. A61K 31/38; C07D 333/00
[52] U.S. Cl. ...................................... 514/447; 549/68

[58] Field of Search ........................... 424/275; 549/68

[56] References Cited

U.S. PATENT DOCUMENTS 4,317,915  3/1982  Confalone et al. .................. 549/68

FOREIGN PATENT DOCUMENTS 1945964  3/1971  Fed. Rep. of Germany ........ 549/68

Primary Examiner—Alan Siegel
Attorney, Agent, or Firm—Raymond A. McDonald; Stephen L. Nesbitt; Gary D. Street

[57] ABSTRACT

This application relates to 4-amino-4,5-dihydro-2-thiophenecarboxylic acid, the $C_{1-6}$ alkyl esters thereof and to their use in the treatment of epilepsy.

9 Claims, No Drawings

α-AMINOBUTYRIC ACID TRANSAMINASE INHIBITORS

CROSS-REFERENCE TO RELATED APPLICATION

This is a continuation of application Ser. No. 597,786, filed Apr. 6, 1984, which is a continuation of application Ser. No. 540,744, filed Oct. 11, 1983, both now abandoned.

This invention relates to 4-amino-4,5-dihydro-2-thiophenecarboxylic acid, esters thereof, and pharmaceutically acceptable salts thereof, to their use as chemotherapeutic agents, and to the chemical processes and intermediates useful in the preparation thereof.

More specifically, this invention relates to γ-aminobutyric acid transaminase inhibitors useful in the treatment of epilepsy. These inhibitors are of the formula

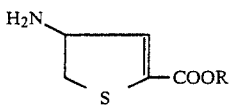

inclusive of their individual enantiomers and racemic mixtures thereof, and the pharmaceutically acceptable salts thereof, wherein R is hydrogen or lower alkyl. Preferably, the lower alkyl moiety contain 1-6 carbon atoms.

The preparation of the compounds of this invention may be achieved by the judicial selection of the appropriate starting material followed by th application of standard chemical reactions and techniques analogously known in the art.

The preparation of the desired compounds is preferentially effected by a series of chemical reactions starting with derivatives of cysteine. In one such process, the amine moiety of 1-ethoxycarbonyl-2-mercaptoethanaminium chloride is converted to its t-butoxycarbonyl derivative by reaction with di-t-butyl dicarbonate and the resulting product is treated with ethylbromoacetate, in situ, to form the desired N-[(1,1-dimethylethoxy)carbonyl]-S-(2-carboethoxyethyl)cysteine ethyl ester derivative. Of course, other N-protecting groups may similarly be employed. The so-prepared cysteine ethyl ester derivative is then subjected to a cyclization reaction using Dieckmann reaction conditions, preferably employing lithium diisopropylamide although others may similarly be utilized. The resulting β-ketoester (i.e., ethyl-4-[[(1,1-dimethylethoxy)carbonyl]amino]tetrahydro-3-oxo-2-thiophene carboxylate is sequentially reduced and dehydrated, preferably utilizing sodium borohydride, followed by mesyl chloride and the resulting N-t-butoxycarbonyl-protected 4,5-dihydro-2-thiophene carboxylic acid esters is deprotected according to standard conditions, such as lithium hydroxide hydrolysis, followed by reaction with dry hydrochloric acid gas.

Alternatively, the t-butoxycarbonyl protected cysteine starting material can be silylated (by reaction with chlorotrimethylsilane and bis(trimethylsilyl)acetamide and the resulting product, when cyclized by reaction with freshly prepared lithium tetramethylpiperidine, will form a tetrahydro-2-thiophenecarboxylate bearing a silyl ether and alkyl ether at the 3-position thereof. The silyl ether is then removed by treatment with HF in the presence of tetrabutylammonium fluoride, and the product subjected to chemical reduction, preferably with sodium borohydride, to form the crude 3-hydroxy-N-t-BOC-protected-tetrahydro-2-carboxylate ester. This product may then be subjected to the same dehydration/deprotection reactions previously described to obtain the desired product.

As shown in formula I, the compounds of this invention contain an asymetric carbon atom and thus the products exist in enantiomorphic forms. The preparation of the individually desired enantiomers is effected by utilizing the appropriate isomer of the starting material (e.g., the D- or L-form of the starting cysteine derivative wherein the L-isomer yields the (R) isomer and the D-isomer yields the (S) isomer). In the event discriminating procedures are not utilized, obtention of the desired isomer may be effected according to standard techniques, such as separation of the racemic mixture with optically active acids or by the use of prep columns such as Prep Percol columns.

The following specific examples illustrate the preferred methods of synthesis although such examples are not restrictive of the methodology which can be utilized. Obvious equivalency functioning procedures may be utilized depending upon factors fully appreciated by those skilled in the art.

EXAMPLE I

4-Amino-4,5-dihydro-2-thiophenecarboxylic acid

Step A:
N-[(1,1-Dimethylethoxy)carbonyl](2-carboethoxyethyl)-L-cysteine ethyl ester Trimethylamine 120 ml (0.88 mole) is added dropwise over a 10 minute period to a stirring ice bath cooled solution containing 40.7 g (0.22 mole) of cysteine ethyl ester hydrochloride, 51.0 g (0.227 mole) of di-tert-butyl-dicarbonate, and 400 ml of dry $CH_2Cl_2$ under a positive argon atmosphere. After an additional 20 minutes the cooling bath is removed and the reaction is stirred at 25° C. for 4 hours. The reaction is then once again cooled with an ice bath and 31 ml (0.264 mole) of ethyl bromoacetate is added and allowed to react for 1 hour at 0° C. and 2 hours at 25° C. After removing the bulk of the solvent at reduced pressure the mixture is transferred to a separatory funnel, diluted with 300 ml of ether, and extracted with 200 ml of water. The organic layer is washed successively with 50 ml water and 50 ml brine and dried over $MgSO_4$. Evaporation of the solvent at reduced pressure affords 75.2 g of a light yellow-orange oil suitable for use in Step B.

Step B: Ethyl 4-[[(1,1-dimethylethoxy)carbonyl]amino]tetrahydro-3-oxo-2-thiophenecarboxylate To a solution of LDA [prepared by the addition of 9.8 ml of 1.75M n-BuLi (0.017 mole) to a solution of 2.4 ml of diisopropylamine (0.017 mole) and 15 ml of THF at 0° C.] cooled to −70° C. (dry ice/acetone) under a positive stream of argon is added dropwise over a 5 minute period 2.83 g of the unpurified cysteine derivative in 60 ml of THF. After stirring for 1 hour at −70° C. the reaction is allowed to warm slowly to 20° C. at which point the mixture is poured into a separatory funnel containing 100 ml of ether and sufficient ½ saturated acidic (HCl) brine to adjust the aqueous layer to pH 3 after equilibration. The organic layer is washed with ½ saturated brine, brine and dried over $MgSO_4$.

The solvent is removed at reduced pressure to afford 2.21 g of oil which affords 1.07 g (44% from cysteine ethyl ester) of nearly pure β-ketoester following flash chromatography (5 cm column) on silica gel eluting sequentially with 20, 30 and 40% EtOAc in hexane.

Step C:
4-[[(1,1-dimethylethoxy)carbonyl]amino]-4,5-dihydro-2-thiophenecarboxylic acid To a stirring solution of 5.16 g (0.178 mole) of the racemic β-ketoester in 40 ml of absolute ethanol cooled to $-5°$ to $-10°$ C. (ice/methanol bath) is added 340 mg (0.009 mole) of $NaBH_4$. After 25 minutes 5 ml of acetone is added and stirring and cooling is continued for an additional 20 minutes. The reaction mixture is then shaken in a separatory funnel containing 200 ml of EtOAc and 50 ml of ½ saturated brine, washed brine, and dried over $MgSO_4$. The solvent is removed under reduced pressure to afford 5.25 g of the crude alcohol.

To a stirring ice bath cooled solution of the above alcohol, 8.3 ml (0.06 mole) of $Et_3N$, and 60 ml of $CH_2Cl_2$ under positive argon pressure is added dropwise 2.1 ml (0.027 mole) of MsCl. After stirring for 2.5 hours at 0° C. the reaction which was judged complete by TLC is poured into 200 ml of ether, washed successively with $3\times30$ ml water and brine, and dried over $MgSO_4$. The unsaturated ester so obtained after removal of the solvent at reduced pressure is dissolved in 60 ml ethanol. To the stirring ice bath cooled solution is added 25 ml of 1N LiOH. After 1 hour at 0° C. the reaction is poured into a separatory funnel containing 150 ml of EtOAc, 70 ml of brine, and 25 ml of 1N HCl and extracted. The separated aqueous layer is re-extracted with 30 ml of fresh EtOAc, and the combined organic layer is washed with 70 ml of brine and dried over $MgSo_4$. The solvent is removed under reduced pressure and the residue purified by flash chromatography (6 cm column) eluting with 30, 38 and 45% EtOAc in hexane containing 1% acetic acid to afford 2.62 g (60% yield) of the crystalline acid, mp. 154°–155° C. A recrystallized (ether/hexane) sample afforded correct combustion analysis. % Calcd: C, 48.96; H, 6.16; N, 5.17; S, 13.07%. % Found: C, 48.85; H, 6.14; N, 5.15; S, 12.99.

Step D: 4-amino-4,5-dihydro-2-thiophenecarboxylic acid

An ice bath cooled solution containing 2.60 g (10.6 mMole) of the t-Boc acid in 100 ml of EtOAc is saturated with dry HCl. The cooling bath is then removed and the reaction is allowed to stand for 1 hour under a positive nitrogen atmosphere. The precipitated solid is collected washed successively with EtOAc and ether to afford, after drying in vacuo at 25° C., 1.20 g of a tan powder composed of amino acid hydrochloride and ammonium chloride. The solid is dissolved in water and the pH adjusted to 8–9 with 2N $NH_4OH$. The solution is then placed on a BioRad AG 50W-X8 ion exchange column (HCl form). The purified amino acid is eluted with 2N $NH_4OH$ and the water removed at reduced pressure (30° C. bath) to afford a tan solid. The solid is transferred to a frit, washed with EtOAc and ether, and dried at high vacuum in a drying pistol (acetone) to afford 556 mg (34% yield) of the analytically pure amino acid. Analysis % Calcd: C, 48.96; H, 6.16; N, 5.71; S, 13.07. % Found: C, 48.85; H, 6.14; N, 5.55; S, 12.99.

EXAMPLE II (S)4-Amino-4,5-dihydro-2-thiophenecarboxylic acid

Step A:
N[(1,1-Dimethoxyethoxy)carbonyl]-N-(trimethylsilyl)-S-(2-carboethoxyethyl)-D-cysteine ethyl ester Into a dry argon-flushed flask containing 12.5 g (37.3 mmoles) of N-[1,1-dimethylethoxy)carbonyl]-S-2-(carboethoxy ethyl)-D-cysteine ethyl ester is added 28 ml (112 mmoles) of bis(trimethylsilyl)acetamide and 0.5 ml (4 mmoles) of chlorotrimethylsilane. The mixture is heated for 7 hours in a 130° C. oil bath and then bulb-to-bulb distilled under a 50 micron vacuum. The 70°–80° C. distilled material is discarded and the 130°–140° C. distilled material is collected to afford 14.0 g of the desired product.

Step B:
Ethyl-4[[(1,1-dimethylethoxy)carbonyl]amino]-3-ethoxy-3-[(trimethylsilyl)oxy]-tetrahydro-2-thiophene carboxylate A 37.5 mmole solution of lithium tetramethylpiperidide (prepared at ice-bath temperature by adding 23.6 ml of 1.58M n-Buli to 7 ml (41 mmole) of 2,2,6,6-tetramethylpiperidine in 50 ml of THF) was added over a 10 minute period to a stirring solution containing 14.0 g (34.4 mmole) of the silylated substrate of Step A in 190 ml THF which was maintained under a positive argon atmosphere at $-65°$ C. Following the addition, the reaction was held for 30 minutes at $-70°$ C. and allowed to warm slowly (~1 hr.) to $-35°$ C. at which point the solution was cooled to $-60°$ C. and quenched with 3.5 ml of acetic acid. The reaction mixture was poured into a separatory funnel containing 300 ml of ether, washed successively with 150 ml water, sufficient 0.5N HCl to afford an acidic aqueous phase, and brine, and dried over $MgSO_4$. Removal of the solvent under reduced pressure afforded 12.4 g of an oil which was purified by flash chromotography (eluting successively with 7.5, 10, 20% EtOAc/Hexanes) to afford 7.53 g of product as a colorless oil.

Step C: Ethyl 4-[[(1,1-dimethylethoxy)carbonyl]amino]tetrahydro-3-hydroxy-2-thiophenecarboxylate Into a stirring 25° C. solution containing 7.53 g (18.5 mmole) of the silyl ether of Step B and 93 ml of a 1M ethanolic HF solution (prepared by mixing 1 part 48% aqueous HF with 29 parts of absolute ethanol) was added 18.5 ml of a 1M solution of tetrabutylammonium fluoride in THF. After stirring for 40 minutes the solution was cooled with an ice/methanol bath and 520 mg (13.6 mmole) of $NaBH_4$ was added portionwise at such a rate that the internal temperature did not rise above 0° C. Following the addition the reaction was stirred for an additional 30 minutes at which point the remaining hydride reagent was destroyed by the addition of 10 ml of acetone. One ml of acetic acid was added after an additional 10 minutes and the reaction was concentrated to a volume of 50 ml under reduced pressure. The concentrated mixture was poured into a separatory funnel containing 300 ml EtOAc and washed successively with 100 ml of ½ saturated brine, $2\times30$ ml water, and 50 ml brine, and dried over $MgSO_4$. Removal of the solvent at reduced pressure afforded 10.4 g of an oil which was used without purification.

Step D:
Ethyl-4-[[(1,1-dimethylethoxy)carbonyl]amino]-4,5-dihydro-2-thiophenecarboxylate Into an ice cooled stirring solution containing the crude alcohol obtained in Step C, 75 ml of CH$_2$Cl$_2$, and 10.5 ml (74 mmole) of Et$_3$N was added 2.9 ml (37 mmole) of mesyl chloride while maintaining the system under a positive argon atmosphere. The reaction was stirred an additional 5 minutes at 0° C. and then 3 hours at 25° C. The reaction was poured into a separatory funnel containing 200 ml Et$_2$O and successively washed with 70 ml water, 1N HCl until the aqueous wash tested acidic; 15 ml water and 50 ml brine, and dried over MgSO$_4$. Removal of the solvent at reduced pressure afforded 6.5 g of a brown oil which was purified by flash chromatography (eluting with 15% and then 20% EtOAc/Hexanes) to yield 3.97 g of product. This material exhibited the following optical rotation $[\alpha]_D^{amb} = +122.8°$ at a concentration of 0.5M in ethanol. The highest rotation observed for the R enantiomer under similar conditions was −128.1°.

Step E:
4-[[(1,1-dimethylethoxy)carbonyl]amino]-4,5-dihydro-2-thiophenecarboxylic acid To a stirring ice cooled solution containing 3.7 g (13.5 mmole) of the ethyl ester in 45 ml of ethanol was added 19 ml of 1N LiOH. After stirring for 1 hour the reaction was extracted in a separatory funnel containing 100 ml EtOAc, 40 ml brine, 20 g ice, and 4 ml of 6N HCl. The organic phase was washed with 2×10 ml H$_2$O and dried over MgSO$_4$. Removal of the solvent under reduced pressure afforded 3.2 g of a crystalline solid, 99% yield. This material was recrystallized from EtOAc/Hexanes to afford 1.2 g of fluffy white crystals. The acid before recrystallization was 99.1% S and 0.9% R.

Step F: 4-amino-4,5-dihydro-2-thiophenecarboxylic acid

The recrystallized acid of Step E (1.2 g) was dissolved in 50 ml EtOAc, cooled with an ice bath, and dry HCl gas was bubbled through the solution for 3 minutes. Ten minutes later the cooling bath was removed. After an additional 1½ hours the reaction was filtered, and the solids washed successively with EtOAc and ether to afford 610 mg of the amino acid hydrochloride as an off white solid.

The sample was purified by ion exchange chromatography (see Step D of Example I) and the aqueous NH$_4$OH solution concentrated under reduced pressure to a volume of 3 to 4 ml. This solution was cooled to 0° and the crystallized free amino acid collected by filtration washing the solid successively with cold ethanol and ether. The solid is dried in vacuo at 40°–50° C. to afford 325 mg of a white crystalline solid. This sample possessed a m.pt. of 202° C. and the following rotation $[\alpha]_D^{amb} = +143.7°$. Analysis of a sample by HPLC showed it to be 99.8% S enantiomer. Elemental Analysis: Calc. C-41.37; H-4.86; N-9.65; S-22.0. Found. C-41.53; H-4.86; N-9.58; S-22.0.

EXAMPLE III

Methyl 4-Amino-4,5-dihydro-2-thiophenecarboxylate HCl

To a stirring argon-flushed solution containing 31 mg (0.21 mmole) of 4-amino-4,5-dihydro-2-thiophenecarboxylic acid and 0.8 ml of methanol was added 175 μl (1.7 mmole) of thionyl chloride. After 2 hours of stirring at 25° C. the solvent was removed in vacuo to afford the crude amino ester as a hydrochloride salt. The NMR of the above material in D$_2$O was consistent with the proposed structure.

Other esters embraced by this application may similarly be prepared by reacting the appropriate alcohol with the amino acid according to the foregoing technique.

Illustrative of the pharmaceutically acceptable salts of the compounds of this invention include nontoxic acid addition salts formed with inorganic acids, such as, hydrochloric, hydrobromic, sulfuric and phosphoric acid, and organic acids such as methane sulfonic, salicylic, maleic, malonic, tartaric, citric, and ascorbic acids; and non-toxic salts formed with inorganic or organic bases such as those of alkali metals, for example, sodium, potassium and lithium, alkaline earth metals, for example, calcium and magnesium, light metals of Group III A for example, aluminum; organic amines such as primary, secondary or tertiary amines, for example, cyclohexylamine, ethylamine, pyridine, methylaminoethanol, ethanolamine and piperazine. The salts can be prepared by conventional means.

As stated above, the compound of this invention possess the inherent characteristics of inhibiting γ-aminobutyric acid transaminase which results in an increase in brain levels of γ-aminobutyric acid. Thus, the compounds are useful in the treatment of disorders of the central nervous system, particularly that dealing with the function of involuntary movement generally associated with seisure disorders of epilepsy.

The ability of the compounds of this invention to inhibit γ-aminobutyric acid transaminase and raise brain GABA levels is determined in vitro by the methods of Lippert et al. (Eur. J. Biochem. 71:441, 1977) and in vivo by Jung et al. (J. Neurochem. 28:717, 1977). γ-Aminobutyric acid levels are markedly increased in mouse brains after treatment with compounds of this invention at doses ranging from 0.5 mg/kg to 10 mg/kg of body weight by parenteral or oral routes. This ability is further demonstrated by the protective effect (anti-epileptic), at doses ranging from 0.5 mg/kg to 25 mg/kg, against convulsions elicited by an intravenous dose of 3-mercaptopropionic acid (100 mg) according to the general method described by Sarhan and Seilar, J. Neuroscience Res., 4 (1979) 399–421 which is used to evidence anti-epileptic activity. Therefore, based on the foregoing results, as well as by comparison with other known compounds useful in the treatment of epilepsy the dose range of the compounds of this invention for the treatment of epilepsy is 0.1 mg–25 mg per kilogram of body weight per day, depending upon the age of the patient, severity of the disease state and other factors as determined by the attending diagnostician.

In addition to their use in the treatment of epilepsy, in their effect on the central nervous system the compounds of the invention may also be used in the treatment of schizophrenia, tardive dyskinesia, muscle spasms and, the compounds also exhibit analgesic effects. Standard laboratory methodology, in conjunction with compounds with known chemotherapeutic agents useful for the foregoing, may readily be utilized to determine the optimal doses for each of these indications.

The compounds of this invention can be administered orally or parenterally to animals, particularly warm blooded animals and mammals and humans either alone or in the form of pharmaceutical preparations containing as the active ingredient compounds of this invention to achieve the desired effect. Pharmaceutical preparations containing compounds of this invention and conventional pharmaceutical carriers can be employed in unit dosage forms such as solids, for example, tablets, pills and capsules or liquid solutions, suspensions or elixirs for oral administration or liquid solutions, suspensions and emulsions for parenteral use. The quantity of compounds administered can vary over a wide range to provide from about 0.1 mg/kg to about 300 mg/kg of body weight of the patient per day. Unit doses of these compounds can contain, for example, from about 50 mg to 2000 mg of the compounds and may be administered, for example, from 1 to 4 times daily. Following are illustrative examples of pharmaceutical preparations containing the compounds of this invention:

|  | Per Tablet |
| --- | --- |
| (a) 4-amino-4,5-dihydro-2-thiophenecarboxylic acid | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following wherein the quantities are on a weight to volume basis:

|  | Amount |
| --- | --- |
| (a) 4-amino-4,5-dihydro-2-thiophenecarboxylic acid | 100.0 mg |
| (b) sodium chloride | q.s |
| (c) water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

An illustrative composition for hard gelatin capsules is as follows:

|  | Amount |
| --- | --- |
| (a) 4-amino-4,5-dihydro-2-thiophenecarboxylic acid | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

We claim:

1. A compound of the formula

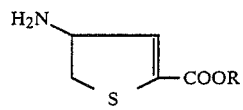

inclusive of the individual enantiomers and racemic mixtures thereof, the pharmaceutically acceptable salts thereof, wherein R is hydrogen and $C_{1-6}$ lower alkyl.

2. A compound of claim 1 wherein R is hydrogen, said compound is 4-amino-4,5-dihydro-2-thiophenecarboxylic acid.

3. The (S) enantiomer of a compound of claim 2.

4. The (R) enantiomer of a compound of claim 2.

5. A compound of claim 1 wherein R is methyl, said compound being methyl 4-amino-4,5-dihydro-2-thiophenecarboxylate.

6. A method for inhibiting γ-aminobutyric acid transaminase in a patient in need thereof which comprises administering an effective amount of a compound of claim 1.

7. A method of treating epilepsy in a patient suffering from epilepsy which comprises administering an antiepileptically effective amount of a compound of claim 1.

8. A method for the treatment of schizophrenia in a patient suffering from schizophrenia which comprises administering an effective amount of a compound of claim 1.

9. A method for the treatment of tardive dyskinesia in a patient suffering thereof which comprises administering an effective amount of a compound of claim 1.

* * * * *